US009078588B2

(12) United States Patent
Ghidoli et al.

(10) Patent No.: US 9,078,588 B2
(45) Date of Patent: Jul. 14, 2015

(54) MRI COMPATIBLE INTRABODY STYLETS AND RELATED METHODS AND SYSTEMS

(71) Applicant: MRI Interventions, Inc., Memphis, TN (US)

(72) Inventors: Daniele Ghidoli, Laguna Hills, CA (US); Kamal Vij, Chandler, AZ (US)

(73) Assignee: MRI Interventions, Inc., Irvine, CA (US)

( * ) Notice: Subject to any disclaimer, the term of this patent is extended or adjusted under 35 U.S.C. 154(b) by 308 days.

(21) Appl. No.: 13/789,868

(22) Filed: Mar. 8, 2013

(65) Prior Publication Data
US 2014/0257086 A1    Sep. 11, 2014

(51) Int. Cl.
| | |
|---|---|
| A61B 5/055 | (2006.01) |
| A61M 25/00 | (2006.01) |
| G01R 33/34 | (2006.01) |
| H01P 11/00 | (2006.01) |
| H01Q 13/00 | (2006.01) |
| G01R 33/28 | (2006.01) |

(52) U.S. Cl.
CPC ............ *A61B 5/055* (2013.01); *A61M 25/0015* (2013.01); *G01R 33/34084* (2013.01); *G01R 33/287* (2013.01); *Y10T 29/49016* (2015.01)

(58) Field of Classification Search
CPC ........... G01R 33/34084; G01R 33/287; G01R 33/34092; G01R 33/343; G01R 33/345; G01R 33/3453; A61M 25/0015
USPC .............. 600/421, 422, 423; 335/299; 29/605
See application file for complete search history.

(56) References Cited

U.S. PATENT DOCUMENTS

| | | |
|---|---|---|
| 6,050,992 A | 4/2000 | Nichols |
| 6,167,311 A | 12/2000 | Rezai |
| 6,284,971 B1 | 9/2001 | Atalar et al. |
| 6,356,786 B1 | 3/2002 | Rezai et al. |
| 6,405,079 B1 | 6/2002 | Ansarinia |
| 6,438,423 B1 | 8/2002 | Rezai et al. |
| 6,526,318 B1 | 2/2003 | Ansarinia |
| 6,539,263 B1 | 3/2003 | Schiff et al. |
| 6,609,030 B1 | 8/2003 | Rezai et al. |
| 6,708,064 B2 | 3/2004 | Rezai |
| 7,561,906 B2 | 7/2009 | Atalar et al. |
| 7,844,319 B2 | 11/2010 | Susil et al. |
| 8,055,351 B2 | 11/2011 | Atalar et al. |
| 8,175,677 B2 | 5/2012 | Sayler et al. |
| 8,320,990 B2 | 11/2012 | Vij |
| 8,374,677 B2 | 2/2013 | Piferi et al. |
| 2008/0243218 A1 | 10/2008 | Bottomley et al. |

*Primary Examiner* — Long V Le
*Assistant Examiner* — Katherine McDonald
(74) *Attorney, Agent, or Firm* — Myers Bigel Sibley & Sajovec, P.A.

(57) ABSTRACT

Intrabody MRI-compatible medical devices with a rigid stylet body with opposing distal and proximal ends with a wall enclosing at least one cavity extending therebetween. The stylet body has first and second laterally spaced apart and opposing external longitudinally extending recessed surfaces and at least one pair of transversely spaced apart apertures extending through the wall and at least one conductor having a length that extends through the cavity then exits the cavity to define at least one external loop extending between the distal end of the stylet body and the pair of transversely spaced apart apertures. First and second legs of each loop snugly abut a respective first and second recessed surface of the stylet body to thereby cooperate with the stylet body to define a substantially cylindrical shape. The at least one conductor with the at least one loop is configured to act as an MRI antenna.

32 Claims, 9 Drawing Sheets

FIG. 9

MRI COMPATIBLE INTRABODY STYLETS AND RELATED METHODS AND SYSTEMS

FIELD OF THE INVENTION

The present invention relates to medical probes and is particularly suitable for use in MRI interventional or diagnostic procedures.

BACKGROUND

MRI is an attractive imaging modality that can be used in MRI guided surgeries. U.S. Pat. No. 8,320,990 describes a flat loop antenna used to obtain high-resolution signal. However, there remains a need for alternative configurations and designs suitable for use in MRI-guided procedures.

SUMMARY OF EMBODIMENTS OF THE INVENTION

Embodiments of the present invention provide MRI compatible stylets that may be particularly suitable for intrabody imaging, such as imaging used during intracardiac, or deep brain diagnostic and/or interventional procedures.

These devices can obtain MRI signals to render MRI images of the local anatomy and may be used to detect and/or measure the electrical pulses of the cranial or other target tissue.

Some embodiments are directed to intrabody MRI-compatible medical devices that have a rigid stylet body with opposing distal and proximal ends with a wall enclosing at least one cavity extending therebetween. The stylet body has first and second laterally spaced apart and opposing external longitudinally extending recessed surfaces and at least one pair of transversely spaced apart apertures extending through the wall. The stylet body also has at least one conductor having a length that extends through the cavity then exits the cavity to define at least one external loop extending between the distal end of the stylet body and the pair of transversely spaced apart apertures. First and second legs of each loop snugly abut a respective first and second recessed surface of the stylet body to thereby cooperate with the stylet body to define a substantially cylindrical shape, and wherein the at least one conductor with the at least one loop is configured to act as an MRI antenna.

The wall at the distal end of the stylet body can have diametrically opposed tip recesses aligned with the longitudinally extending recessed surfaces.

The recessed surfaces can be flat surfaces.

The wall at the distal end of the stylet body can have diametrically opposed arcuate segments neighboring the recesses.

The at least one conductor can have a plurality of segments that snugly abut the recesses.

The stylet body can be formed of alumina.

The at least one conductor can have a tail with leading and trailing ends that extend away from the distal end of the stylet body and are connected to a coaxial cable.

The plurality of external loops can be between 2-10.

The device can also include a tubular member with an outer diameter that corresponds to an outer diameter of the proximal end of the stylet body. The outer diameter can be between about 0.2 inches and about 0.01 inches.

The device may include an internal sleeve that resides inside the stylet body and the tubular member and that encloses a portion of a tail of the conductor and resides away from a coaxial cable attached to the tail of the conductor.

The stylet body can be a monolithic unitary body of non-ferromagnetic ceramic.

The conductor loops can be in communication with at least one capacitor. The loops can have an inductance and the MRI antenna can be tuned to an operating frequency of an MRI scanner using the inductance of the loops and the at least one capacitor.

The loops can have a long side and with a length that is between about 2 mm-10 cm.

The loops have a long side length that is between about 10-50 mm and a lateral side that is between about 0.5 mm to about 10 mm.

The device can also include: (a) an RF decoupling circuit in communication with the antenna configured to isolate the antenna during an MRI excitation RF transmission; and/or (b) a recording splitter circuit in communication with the antenna to decouple the antenna operational mode during a lower frequency mode associated with recording, ablation or stimulation.

The RF decoupling circuit can include a matching and tuning circuit that communicates with an MRI scanner.

The stylet body can be sized and configured as a deep brain probe used for MRI-guided interventional or diagnostic procedures.

Other embodiments are directed to systems for facilitating MR guided neurological procedures. The systems include an intrabrain stylet assembly with a rigid stylet body having opposing distal and proximal ends with a wall enclosing a cavity extending therebetween. The stylet body has first and second laterally spaced apart and opposing external longitudinally extending recessed surfaces and at least one pair of transversely spaced apart apertures extending through the wall and at least one conductor having a length that extends through the at least one cavity then exits the cavity to define a plurality of external loops extending between the distal end of the stylet body and the pair of transversely spaced apart apertures. First and second legs of each loop snugly abut a respective first and second recessed surface of the stylet body to thereby cooperate with the stylet body to define a substantially cylindrical shape. The at least one conductor with the loops is configured to act as an MRI (receive) antenna.

The systems also include an MR scanner interface circuit comprising matching and decoupling circuitry in communication with the MR receive antenna and an MRI scanner.

The system can include a clinician workstation with a display in communication with the stylet assembly configured to display high-resolution MRI images using image data from the probe receive antenna.

The system can include a targeting cannula held by a trajectory guide positioned on a skull of a patient. The stylet assembly can be configured to be held by the targeting cannula during a deep brain procedure.

Still other embodiments are directed to methods of forming an MRI compatible medical stylet. The methods include: (a) providing a rigid non-ferromagnetic stylet body having opposing distal and proximal ends with a wall enclosing a cavity extending therebetween, wherein the stylet body has first and second laterally spaced apart and opposing external longitudinally extending first and second flat surfaces and a pair of apertures extending through the wall; (b) inserting a leading end of the first conductor through the cavity; then (c) turning the leading end back over the first flat surface and defining a first leg of a first loop of an MRI antenna; (d) threading the leading end through the pair of apertures so that a length of the conductor spans across the cavity thereat; then (e) pulling the leading end of the first conductor toward the distal end of the stylet body over the second flat surface thereby forming a second leg of the first loop of the MRI antenna; and (f) repeating the turning, threading and pulling a plurality of times to form multiple loops of the antenna; then (g) directing the leading end of the conductor back into the cavity at the distal end of the stylet body and out the proximal end of the stylet body.

The method can include connecting a tail of the conductor to a coaxial cable; and attaching a tubular member to the proximal end of the stylet body.

The method can be carried out so that the conductor snugly abuts the flat surfaces and recesses on the distal end of the stylet body.

The multiple loops can be between 3-10 loops for a loop length of between about 5 mm to about 50 mm.

Other methods of forming an MRI compatible medical stylet, include: (a) providing a rigid non-ferromagnetic stylet body having opposing distal and proximal ends with a wall enclosing a cavity extending therebetween, wherein the stylet body has first and second laterally spaced apart and opposing external longitudinally extending first and second recessed surfaces and at least one pair of transversely opposing apertures extending through the wall; (b) inserting a leading end of the first conductor through the cavity; then (c) threading the leading end of the first conductor through one of the transversely spaced apart apertures; (d) turning the leading end to extend toward the distal end of the stylet body over the first recessed surface, defining a first leg of a first loop of an MRI antenna; then (e) turning the leading end to abut the distal end of the stylet body; then (f) turning the leading end to extend toward the pair of transversely spaced apart apertures over the second recessed surface thereby defining a second leg of the first loop of the MRI antenna; then (g) threading the leading end through the pair of transverse apertures so that a length of the conductor spans across the cavity thereat; then (h) pulling the leading end of the first conductor toward the distal end of the stylet body over the first recessed surface thereby forming a first leg of a second loop of the MRI antenna; and (i) repeating the threading, turning and pulling a plurality of times to form multiple loops of the antenna; then (j) directing the leading end of the conductor back into the cavity at the distal end of the stylet body or at one the apertures, then out the proximal end of the stylet body.

The systems may be used to guide or view various parts of the body, such as the brain and/or heart during a diagnostic or interventional procedure in substantially real-time MRI.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one stylet or system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms "first" and "second" are used herein to describe various components, regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention.

The term "about" means that the recited number can vary by between +/−20% of the recited number.

The term "stylet" refers to a slender medical probe. In some embodiments, the stylet has a size French between 2 French to 8 French.

The term "MRI compatible" means that the so-called component(s) is suitable for use in an MRI environment and as such is typically made of a non-ferromagnetic MRI compatible material(s) suitable to reside and/or operate in or proximate a conventional medical high magnetic field environment. The "MRI compatible" component or device is "MR safe" when used in the MRI environment and has been demonstrated to neither significantly affect the quality of the diagnostic information nor have its operations affected by the MR system at the intended use position in an MR system. These components or devices may meet the standards defined by ASTM F2503-05. See, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "automatically" means that the operation can be substantially, and typically entirely, carried out without human or manual input, and is typically programmatically directed or carried out. The term "electronically" includes both wireless and wired connections between components. The term "programmatically" means under the direction of a computer program that communicates with electronic circuits and other hardware and/or software.

Embodiments of the invention may be particularly suitable for use with human patients but may also be used with any animal or other mammalian subject.

Embodiments of the present invention may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the application and should not be interpreted in an idealized or overly formal sense unless expressly so defined herein.

Stylet assembly embodiments can be configured to obtain signal data for an MR image, record or detect signal from local tissue and/or stimulate any desired internal region of the body or object. The object can be any object. Embodiments of the invention may be particularly suitable for animal and/or human subjects. Some stylet embodiments can be sized and configured for deep brain procedures. Some embodiments can be configured to place stimulation electrodes to stimulate a desired region of the brain and/or sympathetic nerve chain. Other embodiments are directed to MRI-guided cardiac procedures, such as AFIB (atrial fibrillation) treatments. In some embodiments, the stylet can be introduced intravenously into the heart and guided to help identify locations for atrial wall punctures and/or to obtain signal data to generate high resolution images of lesions associated with ablation treatments. Examples of known treatments and/or target body regions are described in U.S. Pat. Nos. 6,708,064; 6,438,423; 6,356,786;

6,526,318; 6,405,079; 6,167,311; 6,539,263; 6,609,030 and 6,050,992, the contents of which are hereby incorporated by reference as if recited in full herein.

The term "loop" refers to a fully closed or nearly closed shape or line associated with an MRI-compatible (non-ferromagnetic) conductor. The term "conductor" and derivatives thereof refer to a conductive trace, filar, wire, lead, (small-diameter) cable, flex circuit or other electrically conductive member. A single conductor may also be configured as a closely spaced bundle of filars or wires. The conductor can be in the form of a single continuous length. The conductor can be formed with one or more discrete filars, wires, cables, flex circuits, bifilars, quadrafilars or other filar or trace configuration, or by plating, etching, deposition, or other fabrication methods for forming conductive electrical paths. The conductor can be insulated. The conductor can also comprise any suitable MRI-compatible (and biocompatible) material such as, for example, MP35N drawn filled tubing with a silver core and an ETFE insulation on the drawn tubing, Nitinol, gold, copper, silver, platinum, iridium, MP35N, tantalum, titanium, L605, gold-platinum-iridium, gold-copper-iridium, gold-platinum, and the like.

The term "high-resolution" refers to images that have increased resolution (better SNR) relative to conventional images or images obtained with surface coils alone (e.g., typically at least about 4x better SNR than images generated using the MRI Scanner without data from the intrabody-antenna 20 provided by the stylet assembly 10).

Embodiments of the present invention may be particularly suitable for use with high-magnetic field MR Scanner systems. The term "high-magnetic field" refers to field strengths above about 0.5 T, typically above 1.0T, and more typically between about 1.5T and 10T. In some embodiments, the field strength can be about 3.0T. MRI Scanners include closed bore and open bore systems. MRI scanners are well known to those of skill in the art and include, for example, the SIGNA 1.5T/3.0T from GE Healthcare: the ACHEIVA 1.5T/3.0T and the INTEGRA 1.5T from Philips Medical System; and the MAGNETOM Avanto, the MAGNETOM Espree, the MAGNETOM Symphony, and the MAGNETOM Trio, from Siemens Medical.

The terms "MRI Scanner and MR Scanner" are used interchangeably to refer to a Magnetic Resonance Imaging system and includes the magnet, the operating components, e.g., RF amplifier, gradient amplifiers and processors that direct the pulse sequences and that may directly or indirectly identify the scan planes.

Figures 1A, 1B, 1C:
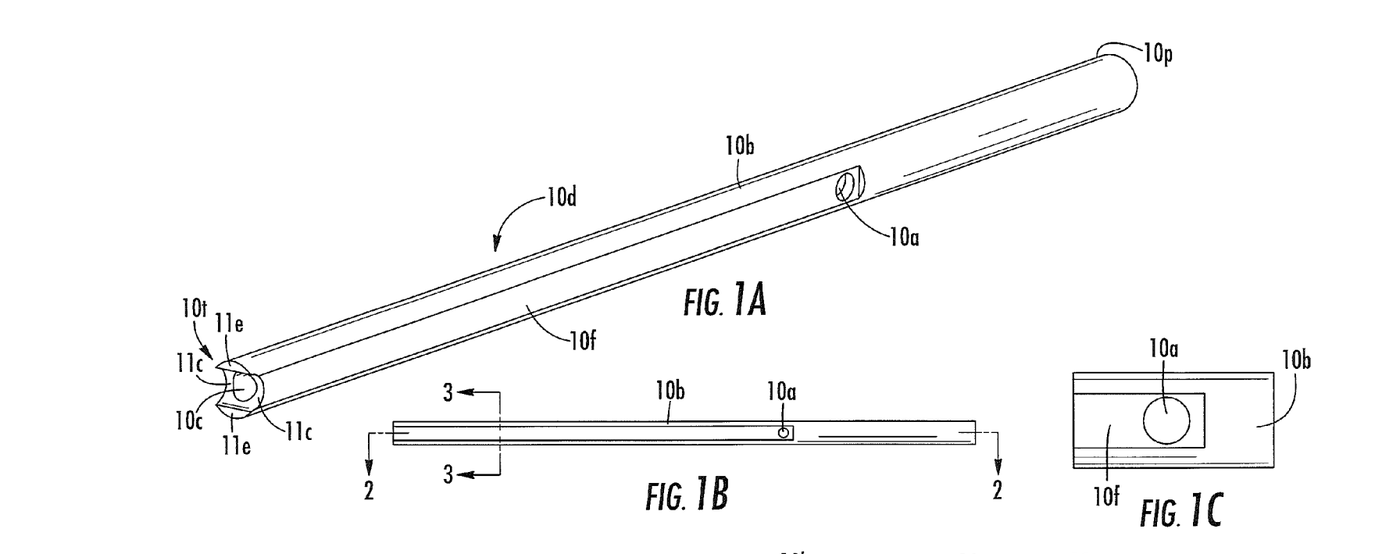
FIG. 1A is a top perspective view of an MRI compatible stylet body according to embodiments of the present invention.
FIG. 1B is a side view of the stylet body shown in FIG. 1A.
FIG. 1C is an enlarged view of a region of the stylet body shown in FIG. 1A according to embodiments of the present invention.
Figure 3:
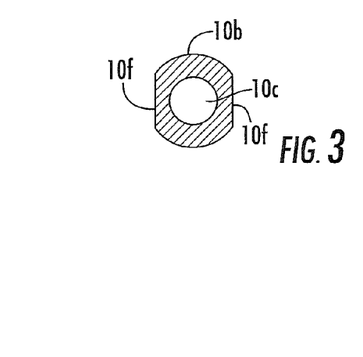
FIG. 3 is a section view of taken along line 3-3 in FIG. 1A.

FIGS. 1A-1C illustrate a stylet 10b according to embodiments of the present invention. The stylet body 10b has a distal end portion 10d which includes first and second external longitudinally extending recessed surfaces 10f and an interior longitudinally extending cavity 10c. In some embodiments, the recessed surfaces 10f can be flat surfaces, but other recessed shapes may be used. The recessed surfaces 10f can extend for between about 5 mm to about 30 cm, typically between about 10 mm to about 12 cm, and more typically between 10 mm to 50 mm. As shown in FIG. 3, the recessed surfaces 10f can be configured as two longitudinally extending outer flat surfaces on opposing sides of the stylet body 10b.

As shown in FIGS. 1A-1C and 2, for example, the recessed surface(s) 101 can have a leading end that extends to the tip 10t of the body 10b and the other end can end proximate at least one transversely extending through-aperture 10a. The aperture 10a can allow a conductor 15 to extend therethrough as will be described further below. The aperture can be circular or have another shape. The aperture 10a can be between about 0.01-0.040 inches in diameter or width/height. Typically, there are two aligned laterally spaced apart apertures 10a.

Referring again to FIG. 1A, the tip 10t can be configured so that the flat surface(s) 10f merge into a curved recess 11c while the opposing edges 11e extend out a distance forward of the curved recess 11c.

The inner cavity 10c can have a width that is between about 0.010 to about 0.050 inches. The cavity 10c can be sized and configured to accommodate first and second legs $15_1$, $15_2$ of a conductor 15 so that the stylet body 10b holds a plurality of conductor loops $15l_1$-$15l_n$, where n=the number of loops (FIG. 4D), shown as 3 in FIG. 4D. In some particular embodiments, the cavity 10c is cylindrical with a diameter that is about 0.031 inches.

The stylet body 10b can have an outer diameter that is between 2-8 French as noted above. In some embodiments, the stylet body 10b has an outer diameter of between about 0.1 and about 0.05 inches, such as about 0.05 inches, about 0.061 inches, and about 0.070 inches.

The stylet body 10b can be rigid and formed of an MRI compatible and biocompatible material such as a non-ferromagnetic metal, composite, sufficiently rigid polymer or ceramic. According to some embodiments, the MRI-compatible material is a ceramic. Suitable ceramics include Alumina. Other MRI-compatible materials that may be used may include glass, fused silica or rigid polymers.

Figure 2:
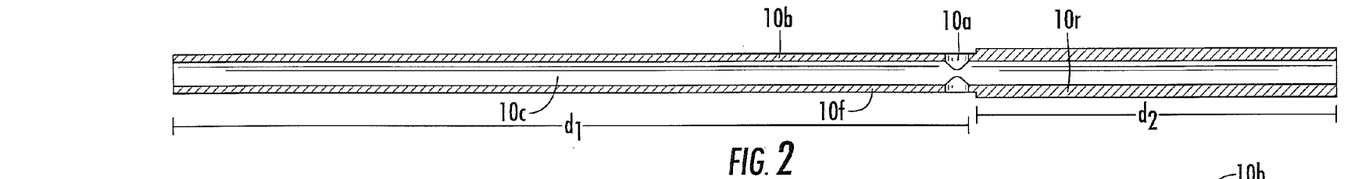
FIG. 2 is a section view of taken along line 2-2 in FIG. 1A.

As also shown in FIGS. 1A, 1B and 2, the stylet 10 includes a first distal segment with a length "$d_1$" that merges into a second segment with a length "$d_2$". The first segment length is typically greater than the second segment length, e.g., $d_1 > d_2$, typically between 2-10 times greater in length. The first segment has the flat outer surfaces 10f while the second segment is cylindrical with a circular profile. The inner diameter associated with the cavity 10c can be constant through the stylet body 10b while the outer diameter can be stepped down a defined distance on two sides forming the recesses 10f while leaving the other two sides in an arcuate configuration.

The stylet body 10b can be a monolithic unitary cylindrical member that is modified to include the recessed surfaces 10f, e.g., the flat surfaces 10f can be milled, etched, shaved, molded or otherwise formed into the distal end of the stylet body 10b.

Figure 4A:
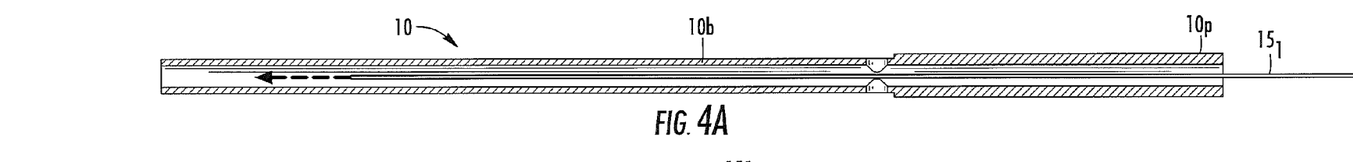
FIGS. 4A-4D are schematic illustrations of the section view of the device shown in FIG. 3 illustrating a sequence of steps that can be used to form conductive loops for an MRI antenna according to embodiments of the present invention.
Figures 4B, 4C:
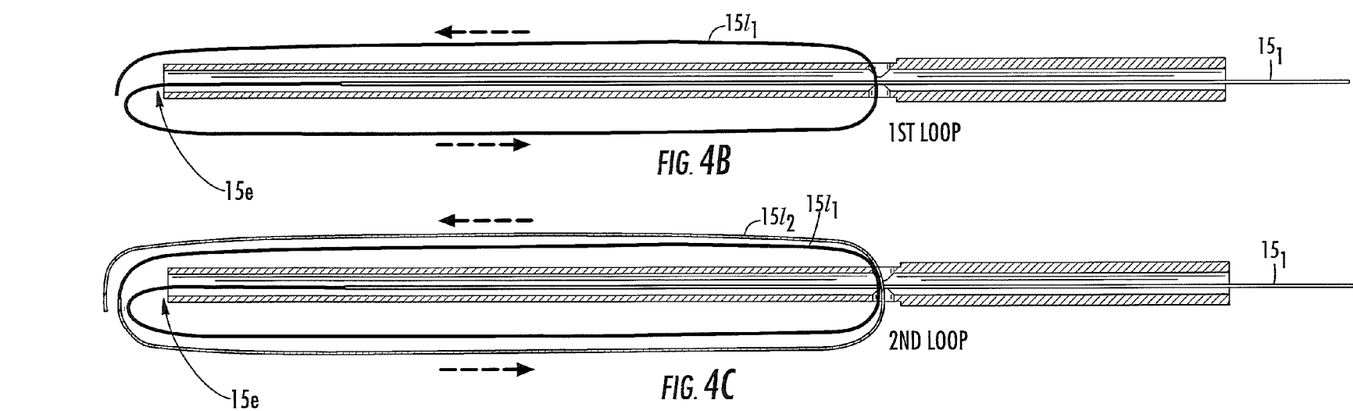

Turning now to FIGS. 4A-4B, the stylet body 10b can have at least one cavity that can be configured to hold at least one loop of 15l of at least one conductor 15. As shown, the stylet 10 can hold a plurality of longitudinally extending loops 15l of a single conductor that cooperate to form an MRI signal receive antenna 20.

The cavity 10c can be a single cavity or may be a segmented into a plurality of cavities. The cavity can be sized and configured to accommodate first and second legs $15_1$, $15_2$ of a conductor 15 so that the stylet body 10b holds a plurality of conductor loops $15l_1$-$15l_n$, where n=the number of loops (FIG. 4D), shown as 3 in FIG. 4D. The number of loops "n" can be between 1 and 100, typically between 2-20, and more typically between 3-10, such as 3, 4, 5, 6, 7, 8, 9 and 10. The stylet body 10b and loops 15l held snugly against the flat surfaces 10f can be configured so that the stylet 10 with at least one conductor 15 has a form factor that simulates a cylindrical stylet.

Figure 4D:
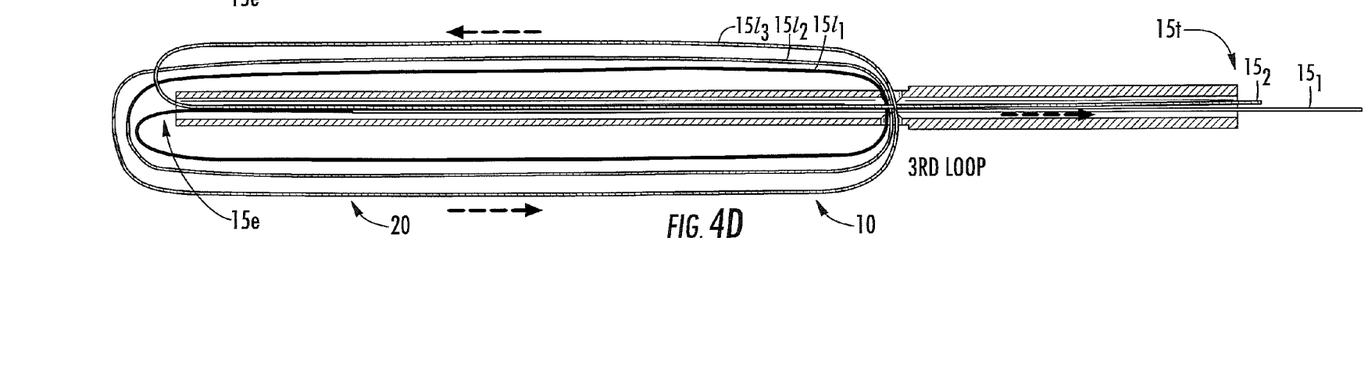

Although not shown, the stylet body 10b can include more than one pair of cooperating apertures, e.g., the body can also include longitudinally spaced apart apertures 10a. Different loops can be configured to extend through different opposing or laterally spaced apart apertures (providing different loop lengths) rather than having each loop extend through a common aperture as shown in FIGS. 4B-4D. Similarly, while the pair of apertures can be aligned across the cavity, they may alternatively be offset so that one leg of a respective loop has a longer length than another (not shown).

Figure 5A:
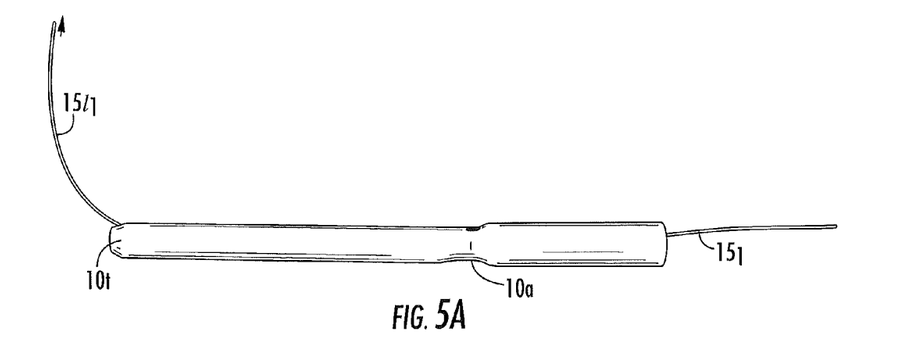
FIGS. 5A-5I are also schematic illustrations of a series of assembly steps that can be carried out to fabricate a stylet assembly according to embodiments of the present invention.
Figure 5B:
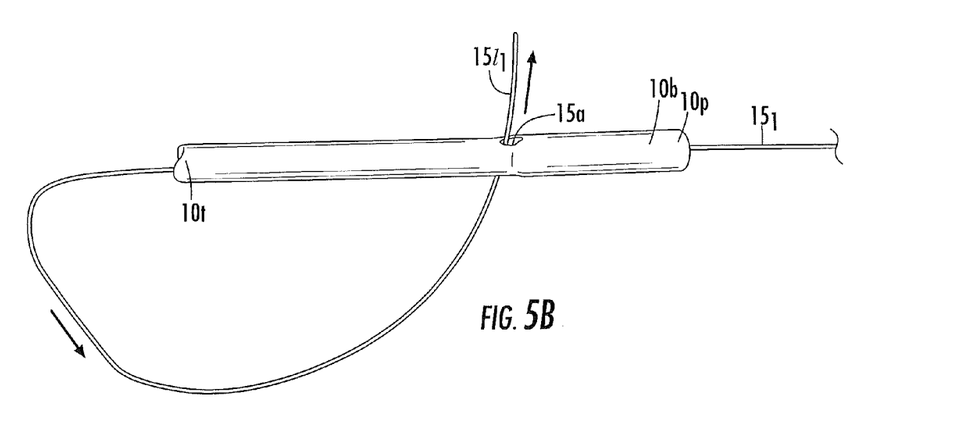

FIGS. 4A-4D and 5A-5C illustrate a sequence of operations that can be used to form the conductor into loops about the stylet body $10b$. As shown in FIGS. 4A and 5A a leading end of the conductor 15 is inserted through the cavity $10c$ and out the tip $10t$ of the stylet body $10b$. This leading end is then directed back and inserted through aperture $10a$ as shown in FIGS. 4B and 5B forming a leg of a loop $15l$ on one side of the stylet body $10b$ against the flat surface $10f$, then pulled forward to form the second leg of the respective loop $15l$ against the other side of the stylet body $10b$ against the other flat surface $10f$. The leading end $15e$ of a respective loop can be held snugly against the wall of the recess $11r$, e.g., inside the recess $11r$ (FIG. 1A).

Figure 5C:
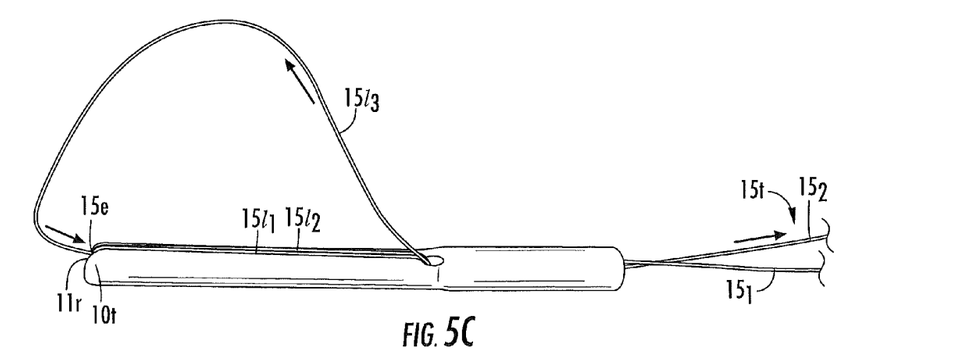
Figure 5D:
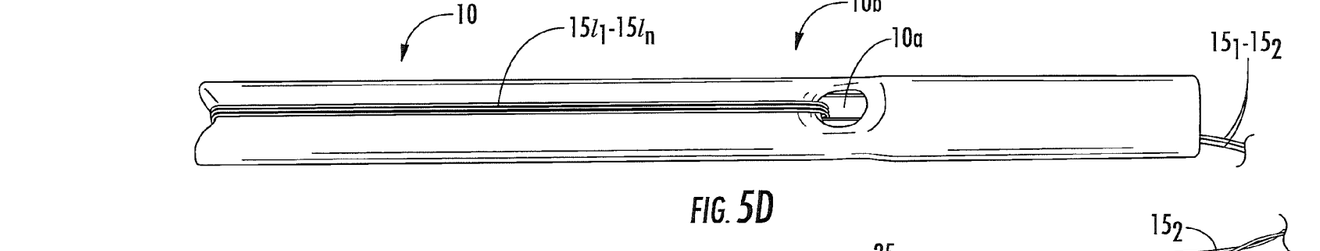
Figure 5E:
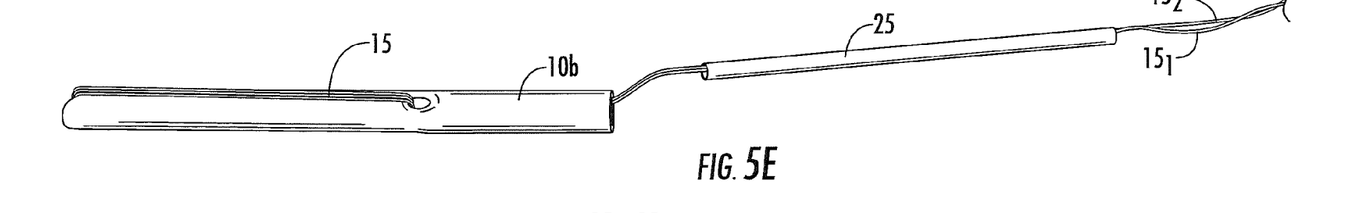
Figure 5F:
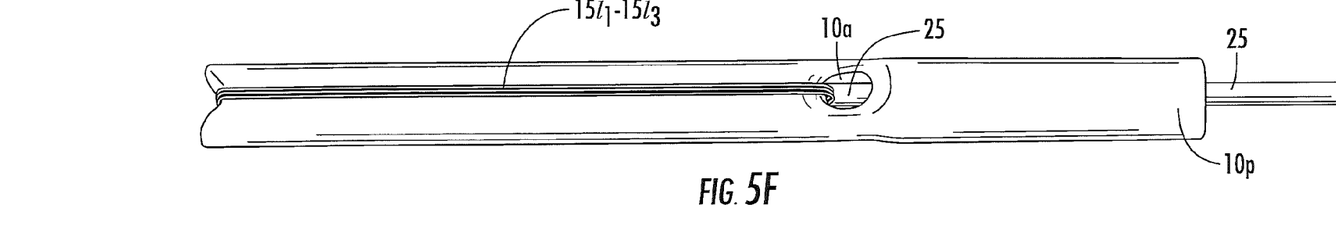
Figure 5G:
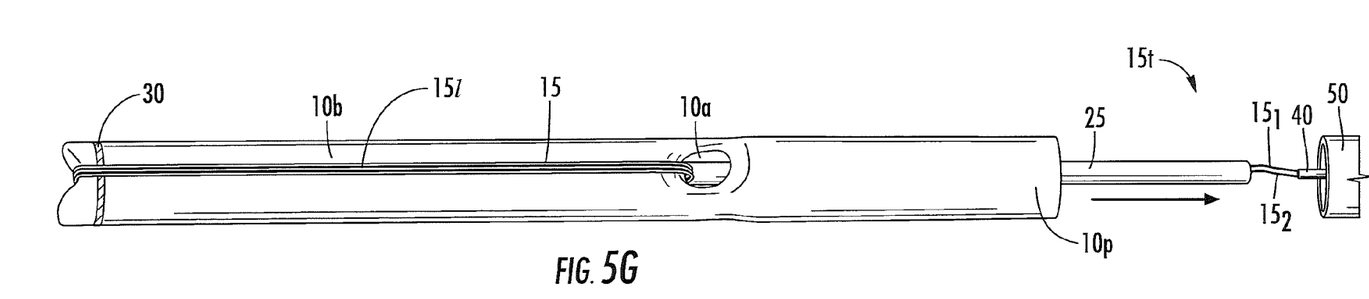
Figure 5H:
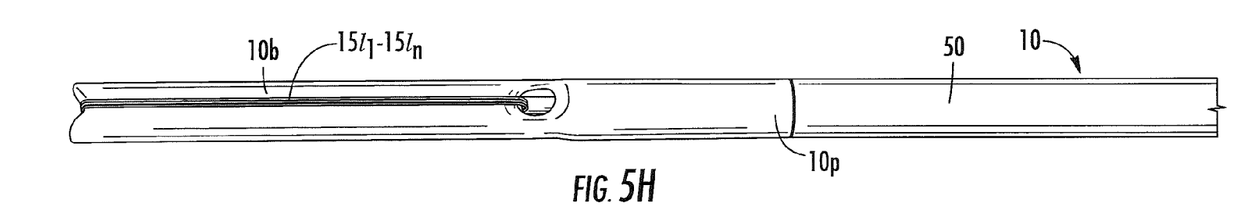
Figure 6:
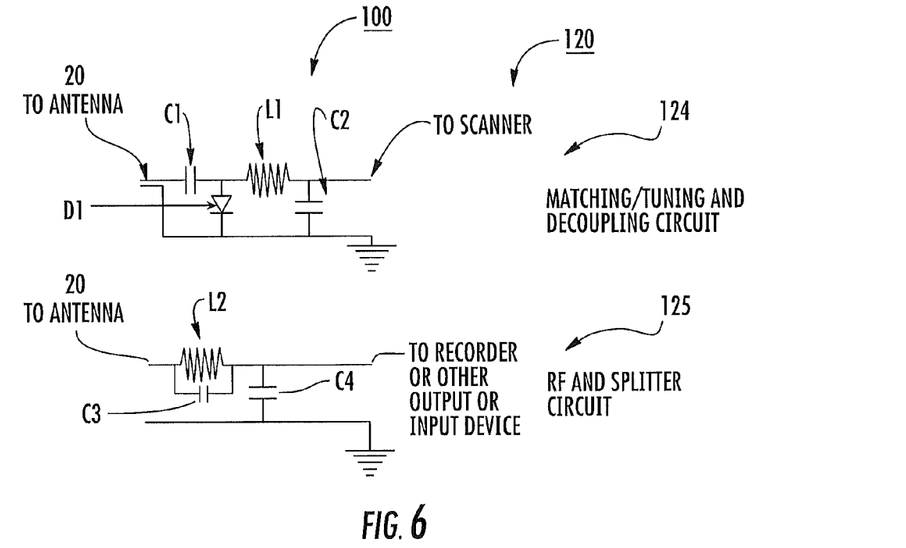
FIG. 6 is a schematic illustration of a matching tuning decoupling circuit and an RF-electrode splitter circuit that can be operatively associated with an MRI compatible stylet assembly according to embodiments of the present invention.

FIGS. 4C and 5C illustrate that this step can be repeated for a desired number of loops, with the conductor 15 threaded through the aperture $10a$ a plurality of times so that there is a closely spaced, typically abutting arrangement of the conductor extending across the stylet aperture $10a$ as shown in FIG. 4D. After the last loop is formed, shown as $15l_3$, the end of the conductor $15_2$ is inserted back into the cavity $10c$ at the tip $10t$ and pulled back down the cavity $10c$ out the other end of the stylet as shown in FIGS. 4D and 5C. The leading and trailing conductor legs $15_1$, $15_2$, respectively (collectively "the tail"), extend to the proximal portion of the stylet body or assembly and define an electrical transmission path to upstream circuitry (e.g., matching/tuning circuit, decoupling circuit, and the like). For example, these two lengths of conductor $15_1$, $15_2$ extend away from the loops $15l$ toward the proximal end of the device $10b$ and can be connected to a coaxial cable 40 as shown in FIG. 5G, then to a decoupling and/or operational circuit 120, 125 (FIG. 6).

Figure 4E:
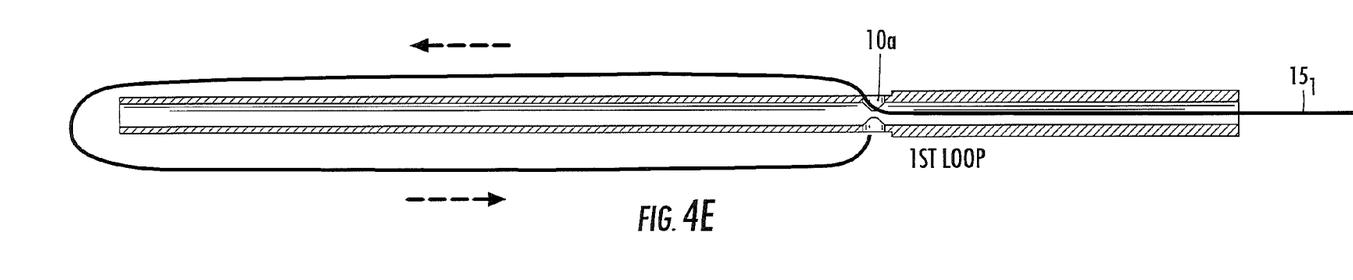
FIGS. 4E and 4F are schematic illustrations of the section view of the device shown in FIG. 3 illustrating an alternate sequence that can be used to form conductive loops for an MRI antenna according to embodiments of the present invention.
Figure 4F:
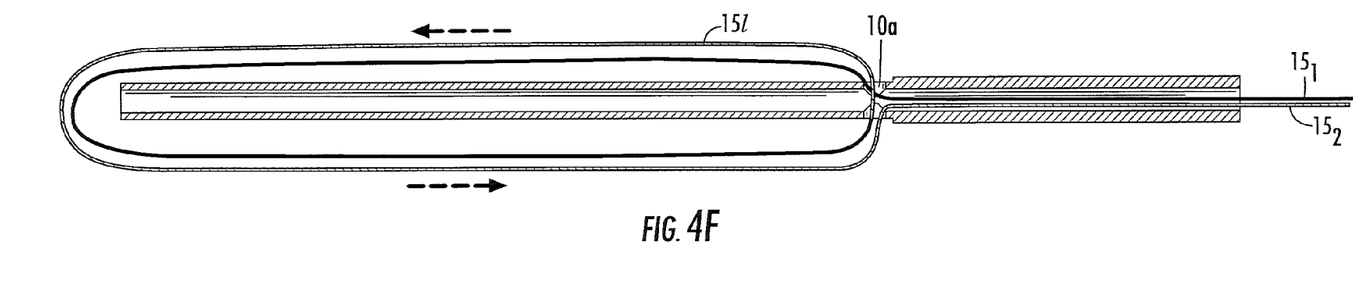

FIGS. 4E and 4F illustrate a modified version of the sequence shown in FIGS. 4A-4D. In this embodiment, the leading end $15e$ first exits one of the side apertures $10a$, then extends out over a first recessed surface $10f$, turns over the tip $10t$, then extends back over the second recessed surface $10f$. For a single loop, the leading end of the conductor $15e$ can reenter the cavity $10c$ and exit the proximal end of the body $10b$. For additional loops, the leading end $15e$ of the conductor can extend through both apertures $10a$, across the cavity $10c$ and loop around the exterior surfaces again so that respective first and second legs of an antenna loop reside against corresponding first and second longitudinally extending recessed surfaces $10f$. The leading end $10e$ can then typically reenter the cavity $10c$ at the distal end $10d$ or via one of the apertures $10a$ to then exit the stylet body $10b$.

FIGS. 5E-5I illustrate that the stylet assembly 10 can include a sleeve or tubing 25 can be inserted into the cavity $10c$ of the proximal end of the stylet body $10b$ over the conductor ends $15_1$, $15_2$. The sleeve 25 can extend a distance into the stylet body $10b$ (ending before the aperture $10a$) and can extend outside the stylet body $10b$ a distance. The coaxial cable 40 can then be attached. The tubing/sleeve 25 can be bonded into a desired position in the stylet body $10b$.

The stylet assembly 10 can also include a tubular member 50 that can be slidably advanced over the conductors $15_1$, $15_2$ and sleeve 25 and attached to the proximal end $10p$ of the stylet body $10b$. The tubular member 50 can also be rigid and may be formed of the same material as the stylet body $10b$.

The tubular member 50 can be the same size and shape as the proximal end of the stylet body $10b$.

It is noted that the sleeve 25 helps hold the components $10b$, 50 together but is not required as other matable configurations may be used including, tongue and groove, rails, channels, bayonet fittings, threaded couplings and the like.

Figure 5I:
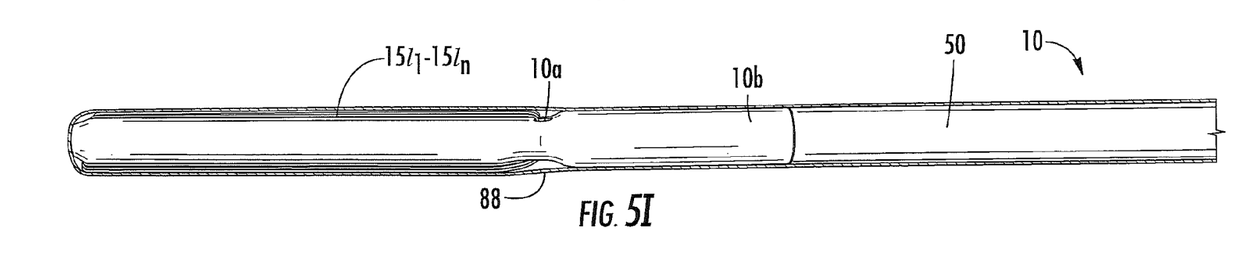

As shown in FIG. 5I, a suitable biocompatible flexible polymeric material 88 can substantially conformably cover the sytlet body $10b$ and external conductor loops 15 and at least part of the tubular member 50. The material 88 can comprise as a molded overlayer, coating or sleeve. The sleeve/material 88 can provide a lubricious smooth outer surface and may provide a safety coating and/or provide a constant outer diameter.

The cavity $10c$ and/or tip $10t$ may be filled or closed with a cap, coating, filling or sleeve.

The assembly 10 can be sterilized so as to meet medical grade sterility standards for medical/surgical procedures.

The antenna 20 formed by the loops $15l$ can be configured to detect/receive MRI signals from a distance that is projected forward from the tip of the body $10t$ by between about 1-2 mm.

The stylet assembly 10 may be configured for intrabody procedures, including, for example, intravenous, intralumen, intracavity or subcutaneous, e.g., deep brain procedures.

As schematically shown in FIG. 5G, for example, the stylet 10 can include at least one electrode 30. The electrode(s) and respective conductor 15 can be electrically insulated from each other and the antenna conductor 15. Each distal electrode 30 can include at least one conductor that is in electrical communication a proximal component, such as a biopotential amplifier or other output or input device. See, e.g., U.S. Pat. No. 8,320,990 for an example of an antenna/electrode configuration, the contents of which are hereby incorporated by reference as if recited in full herein.

As is known to those of skill in the art, where more than one electrodes are used, one electrode can be a reference electrode and another can be a recording electrode for sensing local electrical signal (e.g., potential, voltage and the like). One or more of the electrodes can couple with an external (pad) type electrode (typically attached to a back of a patient) as is well known to those of skill in the art. Thus, for example, two conductors can connect to a biopotential amplifier (the reference and the measuring electrode). In some embodiments, the stylet assembly 10 electrodes 30 can be sized and configured to detect and/or measure cardiac potential and in other embodiments the electrodes are sized and configured to measure and/or detect neural activity (e.g., during deep brain procedures). Where used, a tip electrode can be an ablation or stimulation electrode. As will be discussed further below, the electrode(s) 30 can be in communication with a decoupling circuit. The stylet 10 may not have electrodes, may include only ablation or stimulation electrodes or only recording electrodes and is not required to have either or both types of electrodes. The sensing electrode may also be used as the ablation or stimulation electrode.

Figure 8:
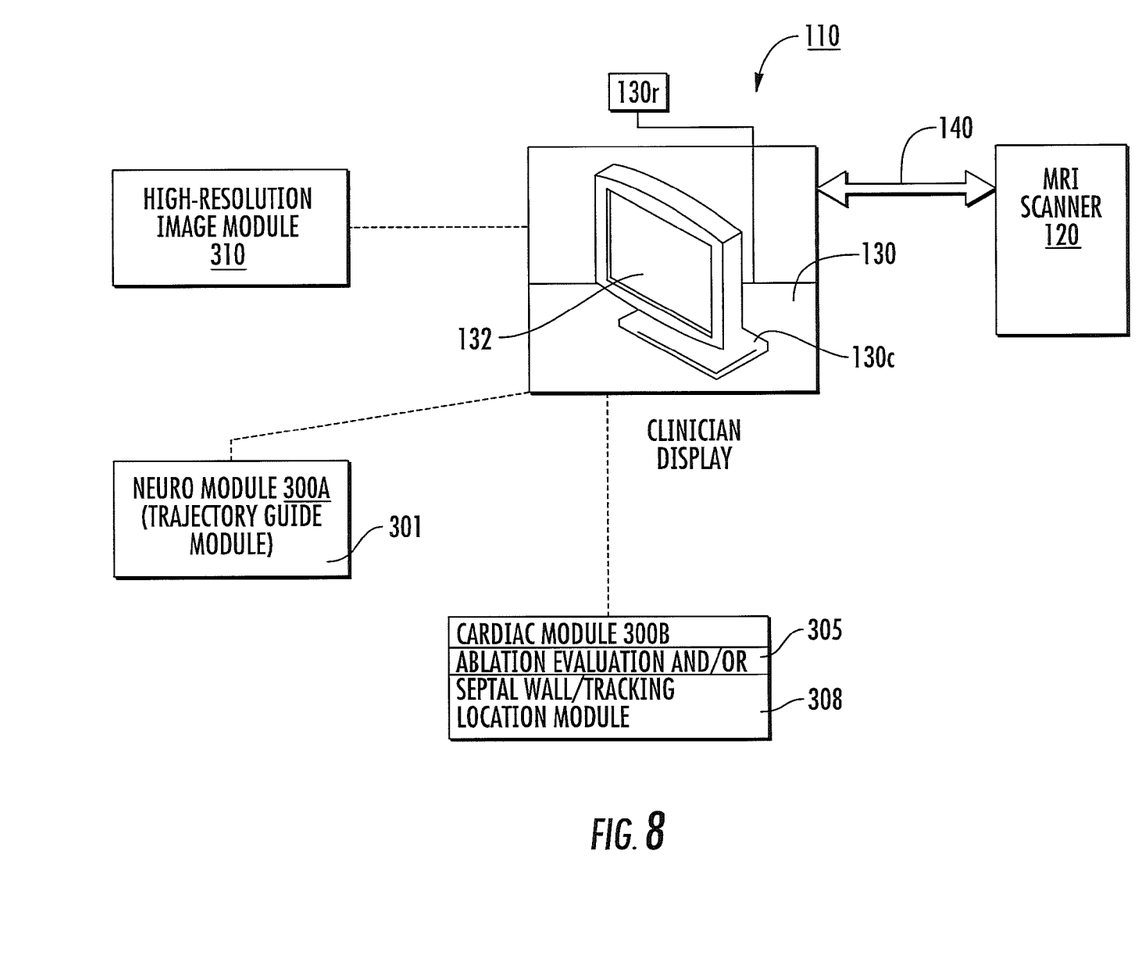
FIG. 8 is a schematic illustration of a system according to embodiments of the present invention.

FIG. 6 illustrates that the stylet assembly 10 can connect to an MRI Scanner interface 100 and can include matching/tuning and decoupling circuit 124 and may optionally be incorporated into a system that communicates with a recorder 125 such as an EP recorder and/or monitor. The matching/tuning and decoupling circuit 124 can be provided as several circuits or integrated into one circuit that communicates with the MR Scanner and stylet assembly 10. Some or all of the components of the circuit 124 can be on the stylet assembly, some or all in a connector associated therewith (not shown) and/or some or all may reside in a separate interface 100 in communication with the Scanner 120 (FIG. 8).

In some embodiments, as discussed above, the stylet assembly 10 can include at least one recording and/or ablating or stimulation electrode $30e$ on a distal portion thereof. In this embodiment, the stylet assembly 10' can define a multi-purpose (e.g., bimodal) device that provides both high frequency (high frequency RF) and low frequency operational modes. For example, decoupling the antenna during micro-electrode recording, ablation or stimulation and/or vice versa, decoupling the electrodes or other components used for recording, ablation or stimulation during RF transmission when the internal MRI antenna 20 is operational in the receive mode (typically electrically isolated so that each mode is not concurrently operative). The low frequency mode may operate in the range of between about 100 Hertz (Hz) to less than about 15 MHz, typically between 100 Hz to about 1 kHz. The high frequency mode typically operates at RF frequencies associated with the operational frequency of the MRI scanner (e.g., about 64 MHz for a 1.5T scanner).

Generally stated, the assembly 10 can be configured so that the MRI RF antenna 20 can be matched and tuned at the MRI operating frequency of interest. The assembly 10 can include or be in communication with a matching/tuning and/or RF decoupling circuit 124 (FIG. 6) as well as a splitter circuit 125 (FIG. 6). The matching/tuning and RF decoupling circuit 124 is configured to decouple the stylet assembly 10 during (high frequency) RF excitation so as to inhibit operation during active RF transmission (activating the antenna to receive MRI signals after RF excitation) associated with the MRI scanner. The splitter circuit 125 can be configured to allow two distinct modes of operation, one which electrically isolates the antenna 20 (to allow low frequency operation, e.g., micro-electric recording (electrophysiology and/or EKG) signal(s), ablation or stimulation of local tissue by the stylet assembly) and the other that allows high frequency operation of the antenna 20. The splitter circuit 125 can include either a high pass and/or a low pass filter. Additional descriptions of suitable circuits are described in U.S. patent application Ser. No. 10/123,534, the contents of which are hereby incorporated by reference. Additional components of the antennas can include RF chokes as described for example, in U.S. Pat. No. 6,284,971, the contents of which are hereby incorporated by reference as if recited in full herein. For additional safety features that can be incorporated into the stylet assembly, see, co-pending U.S. patent application Ser. Nos. 12/090,583; 11/417,594; and 12/047,602, the contents of which are hereby incorporated by reference as if recited in full herein.

In some embodiments, the assembly 10 can have two or three primary operational modes with different electric transmission paths, which are electrically selectively engaged using the splitter circuit 125 (FIG. 6). In operation, during an MRI procedure, an RF excitation pulse is transmitted to a subject. The MRI antenna 20 can be decoupled during RF transmission, then operative during a receive cycle to receive signal from local tissue. The recording and/or ablation or stimulation electrode(s), where used, may also be electrically isolated via the splitter circuit 125 so that only the MRI antenna is active during. MRI signal acquisition by the antenna 20. The assembly 10 can have a proximal connector that connects to an MRI interface that communicates with the MRI scanner or that incorporates the MRI interface and directly connects to the MRI scanner.

During MRI guided clinical procedure, the assembly 10 can first be used as an MRI antenna to provide high resolution imaging of the target internal anatomy (such as neural or cardiac tissue) and/or to locate the position of the electrode or stylet 10b in the body by obtaining MRI signals and hence, images, that are acquired by the external coils and/or internal MRI antenna. As discussed above, one or more (where more than one electrode us used) of the electrodes 30 can also be used to sense and output electrical signals from the target (e.g., neural) anatomy. In other embodiments, the electrodes can be used to deliver therapy such as stimulation or ablation treatments.

Figure 7:
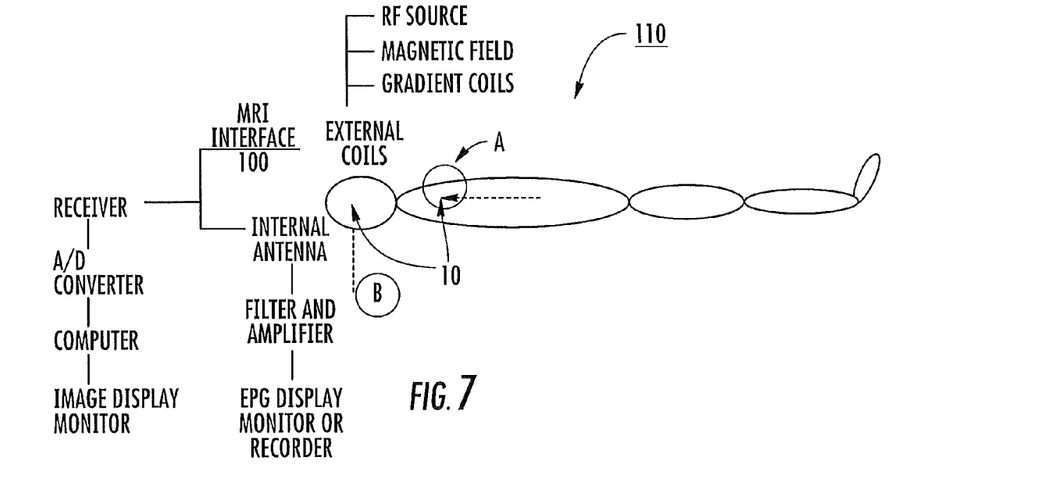
FIG. 7 is a schematic illustration of a system according to embodiments of the present invention.

FIG. 7 illustrates conventional components of an MRI system 110 and the assembly 10. In position "A", the assembly 10 is in the heart of a patient, such as for cardiac treatments according to particular embodiments of the present invention. In this embodiment, the system 110 may include filter and amplifier for monitoring ECG or electrophysiology signals in an MRI environment. In position "B", the assembly 10, is in the brain of the patient according to some embodiments of the present invention.

The imaging assembly 10 can be used in MRI systems for gene and/or stem-cell based therapy delivery or other neural therapy delivery and allow user-defined custom targets in the brain or to other locations (e.g., incorporated into or used with an injection catheter). In addition, embodiments of the systems can be used to ablate tissue in the brain, heart or other locations. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

FIG. 8 illustrates an MRI guided interventional system 110 with an MRI scanner 120, a clinician workstation 130 with at least one circuit 130c, at least one display 132 and the imaging stylet assembly 10. An MRI scanner interface 140 may be used to allow communication between the workstation 130 and the scanner 120. The interface 140 and/or circuit 130c may be hardware, software or a combination of same. The interface 140 and/or circuit 130c may reside partially or totally in the scanner 120, partially or totally in the workstation 130, or partially or totally in a discrete device therebetween. The system 110 can be configured to render or generate real time (high-resolution) visualizations of the target anatomical space using MRI image data. The assembly 10 can include or cooperate with tracking, monitoring and/or interventional components for MRI-guided interventions or diagnosis.

As shown, the system can include a High-Resolution Image Module 310 that can use the MRI signal from the antenna 20 to generate and/or display a high-resolution image. The system may also optionally or alternatively include a Neuro Module 300A and/or a Cardiac Module 300B. The Neuro Module 300A can communicate with or include a trajectory guide module 301 for tracking or visualizing a trajectory and/or local tissue. The Cardiac Module 300B can include an Ablation Evaluation Module 305 (for visualizing displaying lesions created during an MRI procedure) and/or a Septal Wall Tracking Location Module 308 for showing local anatomical tissue and location to facilitate clinical decisions on where to puncture the atrial wall during an intracardiac AFIB procedure, for example.

Figure 9:
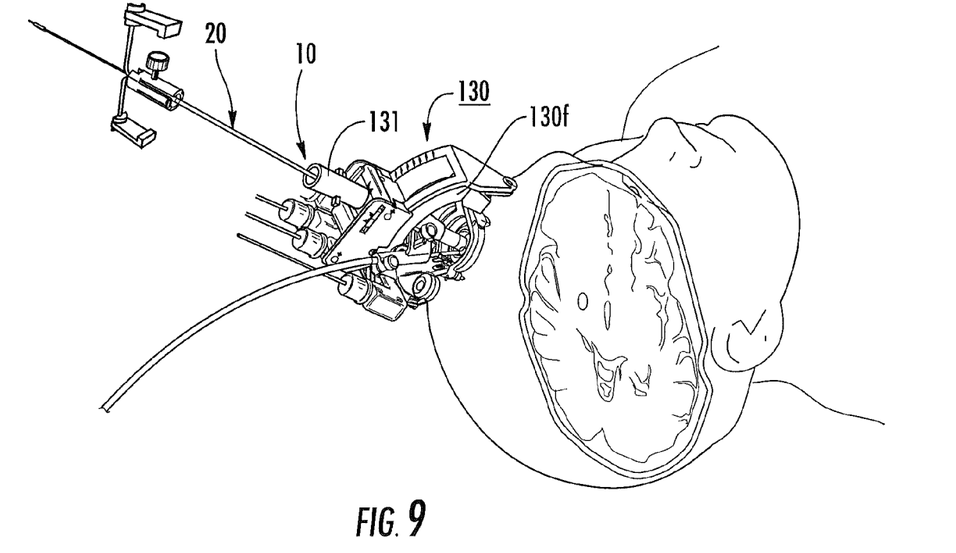
FIG. 9 is a schematic illustration of the stylet assembly used with a targeting cannula according to embodiments of the present invention.

FIG. 9 illustrates the assembly 10 can be used with a trajectory guide 130 having a targeting cannula 131. The guide and targeting cannula can provide X-Y adjustment and pitch and roll adjustment and may be controlled by a trajectory adjustment controller. The frame 130f can include control arcs that cooperate with a platform to provide pitch and roll adjustments. The platform can allow for X-Y adjustments of the trajectory. For additional discussion of suitable trajectory guides, see, U.S. application Ser. No. 12/134,412, and co-pending, co-assigned U.S. patent application Ser. No. 12/236,950, the contents of which are hereby incorporated by reference as if recited in full herein.

Embodiments of the present invention may take the form of an embodiment combining software and hardware aspects, all generally referred to herein as a "circuit" or "module." In some embodiments, the circuits or modules include both software and hardware. Furthermore, certain modules or circuits of the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. Embodiments of the present invention, however, are not limited to any particular programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Computer program instructions may be provided to a processor of a general purpose computer, special purpose computer, ACIS or other programmable data processing apparatus to produce a machine, such that the instructions, which execute via the processor of the computer or other programmable data processing apparatus, create means for implementing the functions/acts specified in the blocks of the block diagrams/schematic illustrations.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The block diagrams of certain of the figures herein illustrate exemplary architecture, functionality, and operation of possible implementations of embodiments of the present invention. In this regard, each block represents a segment or portion of code, which comprises one or more executable instructions for implementing the specified logical function(s).

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An elongate intrabody MRI-compatible medical device, comprising:
    a rigid stylet body having opposing distal and proximal ends with a wall enclosing at least one cavity extending therebetween, wherein the stylet body has first and second laterally spaced apart and opposing external longitudinally extending recessed surfaces and at least one pair of transversely spaced apart apertures extending through the wall; and
    at least one conductor having a length that extends through the cavity, then exits the cavity to define a plurality of external loops extending between the distal end of the stylet body and the pair of transversely spaced apart apertures,
    wherein first and second legs of the external loops snugly abut a corresponding one of the first and second recessed surfaces of the stylet body to thereby cooperate with the stylet body to define a substantially cylindrical shape, and wherein the at least one conductor with the external loops is configured to act as an MRI antenna,
    wherein the at least one conductor with the external loops is configured so that the at least one conductor either extends through the cavity of the stylet body then (a) first exits one of the transversely spaced apart apertures of the stylet body and extends outside the cavity of the stylet body against the first recessed surface, then around the distal end of the stylet body to turn and reside against the second recessed surface, then extends through both transversely spaced apart apertures or (b) first exits the distal end of the stylet body, turns back toward the pair of transversely spaced apart apertures outside the cavity of the stylet body against one of the first or second recessed surfaces, then extends through the pair of transversely spaced apart apertures to exit and extend against the other of the first or second recessed surfaces.

2. The device of claim 1, wherein the recessed surfaces are flat surfaces.

3. The device of claim 1, wherein the wall at the distal end of the stylet body has diametrically opposed tip recesses aligned with the longitudinally extending recesses.

4. The device of claim 3, wherein the wall at the distal end of the stylet body has diametrically opposed arcuate segments neighboring the tip recesses.

5. The device of claim 4, wherein the at least one conductor has a plurality of segments that snugly abut the tip recesses.

6. The device of claim 1, wherein the stylet body comprises a ceramic comprising alumina.

7. The device of claim 1, wherein the at least one conductor has a tail with leading and trailing ends that extend away from the distal end of the stylet body and are connected to a coaxial cable.

8. The device of claim 1, wherein the plurality of external loops is between 2-10.

9. The device of claim 1, further comprising a tubular member attached to that proximal end of the stylet body, the tubular member having an outer diameter that corresponds to an outer diameter of the proximal end of the stylet body, and wherein the outer diameter is between about 0.2 inches and about 0.01 inches.

10. The device of claim 9, further comprising an internal sleeve that resides inside the stylet body and the tubular member and that encloses a portion of a tail of the conductor proximate a coaxial cable attached to the tail of the conductor.

11. The device of claim 9, further comprising an external polymeric sleeve or coating that conformably resides against the stylet body and at least a portion of the tubular member.

12. The device of claim 1, wherein the stylet body is a monolithic unitary body of non-ferromagnetic ceramic.

13. The device of claim 1, wherein the conductor external loops are in communication with at least one capacitor, wherein the external loops have an inductance, and wherein the MRI antenna is tuned to an operating frequency of an MRI scanner using the inductance of the external loops and the at least one capacitor.

14. The device of claim 1, wherein the external loops have a long side with a length that is between about 2 mm-10 cm.

15. The device of claim 14, wherein the external loops have a long side length that is between about 10-50 mm and a lateral side with a length that is between about 0.5 mm to about 10 mm.

16. The device of claim 1, further comprising: (a) an RF decoupling circuit in communication with the antenna configured to isolate the antenna during an MRI excitation RF transmission; and/or (b) a recording splitter circuit in communication with the antenna to decouple the antenna operational mode during a lower frequency mode associated with recording, ablation or stimulation.

17. The device of claim 16, wherein the RF decoupling circuit comprises a matching and tuning circuit that communicates with an MRI scanner.

18. The device of claim 1, wherein the stylet body is sized and configured as a deep brain probe used for MRI-guided interventional or diagnostic procedures.

19. A system for facilitating MR guided neurological procedures, comprising:
(a) an intrabrain stylet assembly comprising:
a rigid stylet body having opposing distal and proximal ends with a wall enclosing at least one cavity extending therebetween, wherein the stylet body has first and second laterally spaced apart and opposing external longitudinally extending recessed surfaces and at least one pair of transversely spaced apart apertures extending through the wall; and
at least one conductor having a length that extends through the at least one cavity then exits the cavity to define a plurality of external loops extending between the distal end of the stylet body and the pair of transversely spaced apart apertures,
wherein first and second legs of at least one loop snugly abut a corresponding one of the first and second recessed surface of the stylet body to thereby cooperate with the stylet body to define a substantially cylindrical shape, and wherein the at least one conductor with the loops is configured to act as an MRI antenna, wherein the at least one conductor of the intrabrain stylet is configured so that the at least one conductor either extends through the cavity then (a) first exits one of the transversely spaced apart apertures of the stylet body and extends outside the cavity of the stylet body against the first recessed surface, then around the distal end of the stylet body to turn and reside against the second recessed surface, then extends through both transversely spaced apart apertures or (b) first exits the distal end of the stylet body, turns back toward the pair of transversely spaced apart apertures outside the cavity of the stylet body against one of the first or second recessed surfaces, then extends through the pair of transversely spaced apart apertures to exit and extend against the other of the first or second recessed surfaces; and
(b) an MR scanner interface circuit comprising matching and decoupling circuitry in communication with the MR receive antenna and an MRI scanner.

20. The system of claim 19, wherein the longitudinally extending recessed surfaces of the intrabrain stylet are flat surfaces.

21. The system of claim 19, wherein the wall at the distal end of the stylet body has diametrically opposed tip recesses aligned with the longitudinally extending recesses, and wherein the wall at the distal end of the stylet body has diametrically opposed arcuate segments neighboring the tip recesses.

22. The system of claim 19, wherein the intrabrain stylet comprises a tubular member that is attached to the proximal end of the stylet body and encloses a portion of a tail of the conductor proximate a coaxial cable attached to the tail of the conductor, wherein the intrabrain stylet further comprises an external sleeve conformably attached to the stylet body and at least a portion of the tubular member, and wherein the external loops have a long side with a length that is between about 2 mm-10 cm.

23. The system of claim 19, further comprising a clinician workstation with a display in communication with the stylet assembly configured to display high-resolution MRI images using image data from the MRI antenna of the stylet.

24. The system of claim 19, further comprising a targeting cannula held by a trajectory guide positioned on a skull of a patient, and wherein the stylet is configured to be held by the targeting cannula during a deep brain procedure.

25. A method of forming an MRI compatible medical stylet, comprising:
providing a rigid non-ferromagnetic stylet body having opposing distal and proximal ends with a wall enclosing a cavity extending therebetween, wherein the stylet body has first and second laterally spaced apart and opposing external longitudinally extending first and second recessed surfaces and at least one pair of transversely opposing apertures extending through the wall;
inserting a leading end of the first conductor through the cavity; then
turning the leading end back over the first recessed surface and defining a first leg of a first loop of an MRI antenna;
threading the leading end through the pair of apertures so that a length of the conductor spans across the cavity thereat; then
pulling the leading end of the first conductor toward the distal end of the stylet body over the second recessed surface thereby forming a second leg of the first loop of the MRI antenna; and repeating the turning, threading and pulling a plurality of times to form multiple loops of the antenna; then directing the leading end of the conductor back into the cavity at the distal end of the stylet body and out the proximal end of the stylet body.

26. The method of claim 25, further comprising connecting a tail of the conductor to a coaxial cable; and attaching a tubular member to the proximal end of the stylet body.

27. The method of claim 25, wherein the recessed surfaces are flat surfaces, and wherein the method is carried out so that the conductor snugly abuts the flat surfaces and recesses on a the distal end of the stylet body.

28. The method of claim 25, wherein the multiple loops are between 3-10 loops for a loop length of between about 2 mm to about 10 cm.

29. A method of forming an MRI compatible medical stylet, comprising:
    providing a rigid non-ferromagnetic stylet body having opposing distal and proximal ends with a wall enclosing a cavity extending therebetween, wherein the stylet body has first and second laterally spaced apart and opposing external longitudinally extending first and second recessed surfaces and at least one pair of transversely opposing apertures extending through the wall;
    inserting a leading end of the first conductor through the cavity; then
    threading the leading end of the first conductor through one of the transversely spaced apart apertures;
    turning the leading end to extend toward the distal end of the stylet body over the first recessed surface, defining a first leg of a first loop of an MRI antenna; then
    turning the leading end to abut the distal end of the stylet body; then
    turning the leading end to extend toward the pair of transversely spaced apart apertures over the second recessed surface thereby defining a second leg of the first loop of the MRI antenna; then
    threading the leading end through the pair of transverse apertures so that a length of the conductor spans across the cavity thereat; then
    pulling the leading end of the first conductor toward the distal end of the stylet body over the first recessed surface thereby forming a first leg of a second loop of the MRI antenna; and
    repeating the threading, turning and pulling a plurality of times to form multiple loops of the antenna; then
    directing the leading end of the conductor back into the cavity at the distal end of the stylet body or at one the apertures, then out the proximal end of the stylet body.

30. The method of claim 29, further comprising connecting a tail of the conductor to a coaxial cable; and attaching a tubular member to the proximal end of the stylet body.

31. The method of claim 29, wherein the recessed surfaces are flat surfaces, and wherein the method is carried out so that the conductor snugly abuts the flat surfaces and recesses on a the distal end of the stylet body.

32. The method of claim 29, wherein the multiple loops are between 3-10 loops for a loop length of between about 2 mm to about 10 cm.

* * * * *